United States Patent [19]

Mayclin

[11] Patent Number: 4,997,370
[45] Date of Patent: Mar. 5, 1991

[54] DENTAL MODEL ALIGNMENT DEVICE

[76] Inventor: Thomas J. Mayclin, 5705 Dale Ave., Edina, Minn. 55436

[21] Appl. No.: 412,573

[22] Filed: Sep. 25, 1989

Related U.S. Application Data

[63] Continuation of Ser. No. 140,073, Dec. 31, 1987, abandoned.

[51] Int. Cl.$^5$ .............................................. A61C 19/00
[52] U.S. Cl. ...................................................... 433/74
[58] Field of Search .......................................... 433/74

[56] References Cited

U.S. PATENT DOCUMENTS

| | | | |
|---|---|---|---|
| 3,153,283 | 10/1964 | Weissman | 433/74 |
| 3,470,614 | 10/1969 | Kelly | 433/74 |
| 3,798,772 | 3/1974 | Eberhard | 433/74 |
| 4,205,443 | 6/1980 | Weissman | 433/74 |
| 4,300,884 | 11/1981 | Camacho | 433/74 |
| 4,321,036 | 3/1982 | Weissman | 433/74 |
| 4,363,625 | 12/1982 | der Avanessian | 433/74 |

OTHER PUBLICATIONS

Product literature from Darby Dental Laboratory Supply Co., Inc., Page 49.
Product literature from Whaledent for a "Pindex System", Page 82.
Product literature from Denerica Dental Corporation, Page 33.
Product literature from Protect-O-Bubble.

*Primary Examiner*—John J. Wilson
*Attorney, Agent, or Firm*—Gregory P. Kaihoi

[57] ABSTRACT

A mounting and alignment device for removably mounting a dental model or portion thereof to a base cast. The device comprises an alignment collar which is adapted to be fixedly secured to a dowel pin and a dental model, the combination being receivable in a complimentary depression in a base cast to align and retain the dental model, preventing it from rotating or moving transversely with respect to the base cast when the portions are cooperatively engaged. A gasket may be included in the base cast to further enhance the engagement between the dowel pin and the base cast.

8 Claims, 3 Drawing Sheets

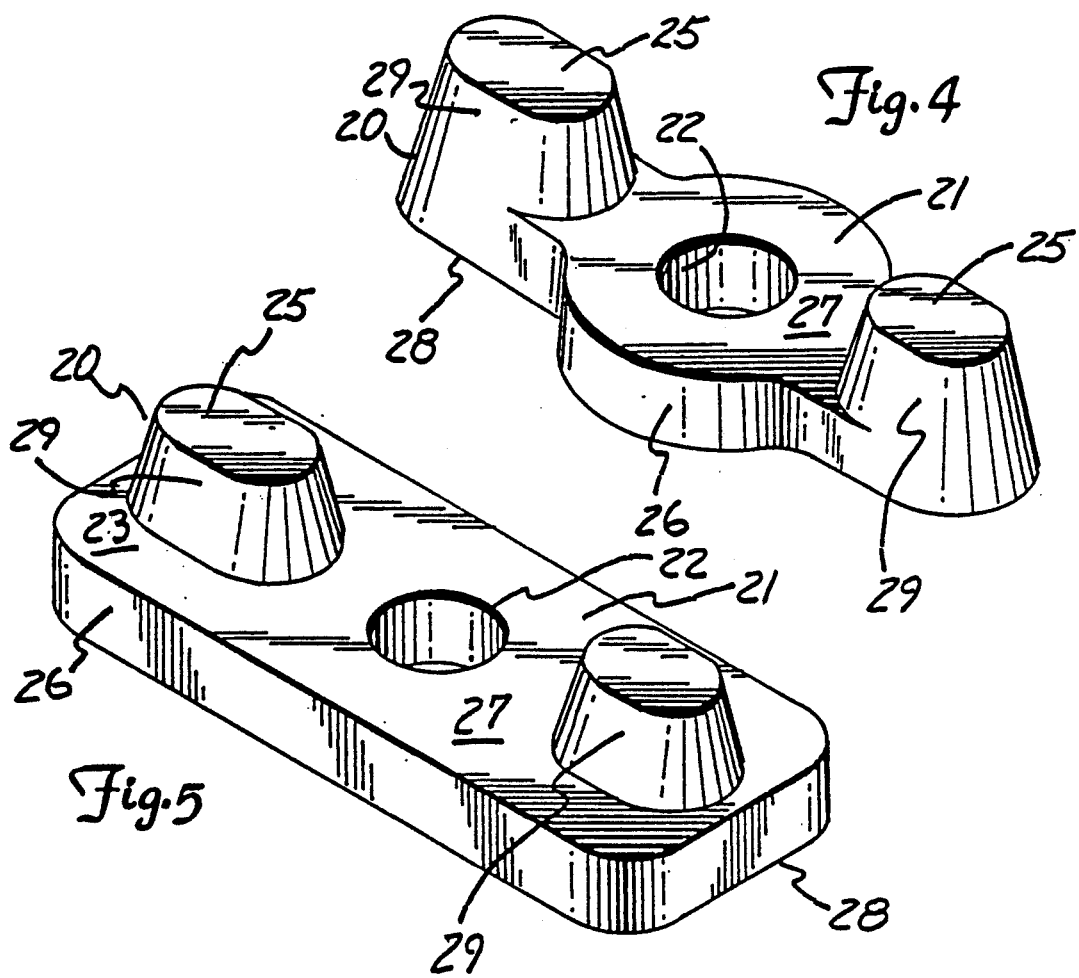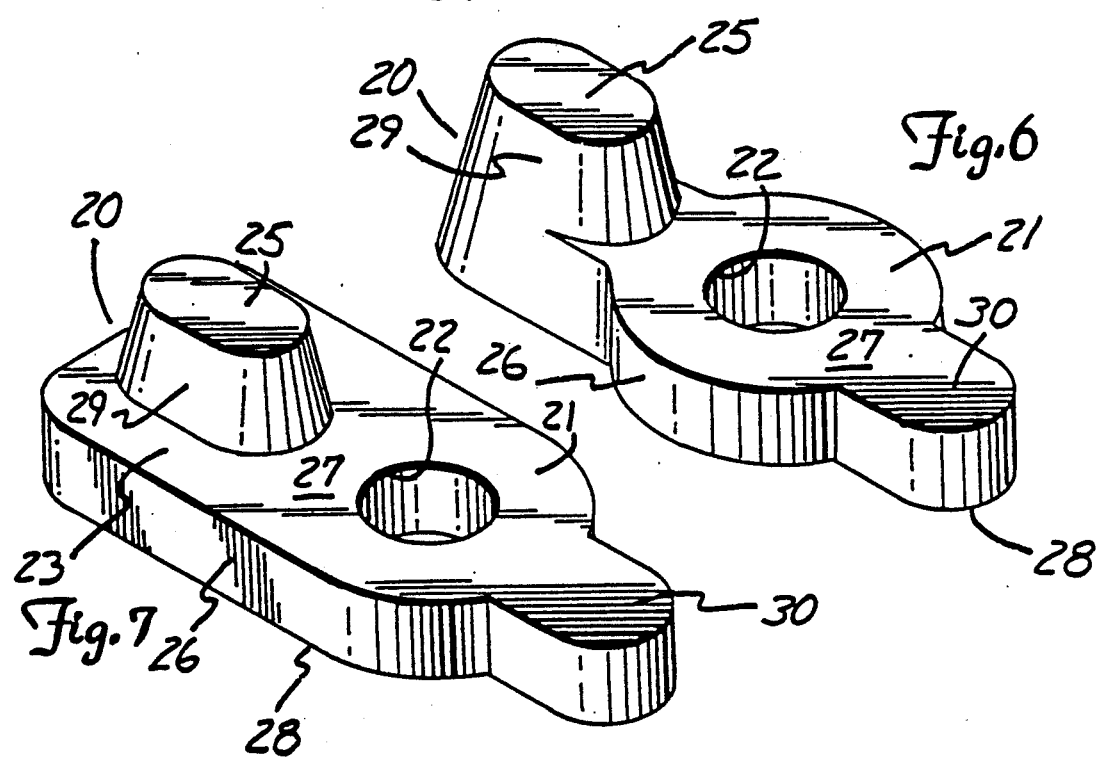

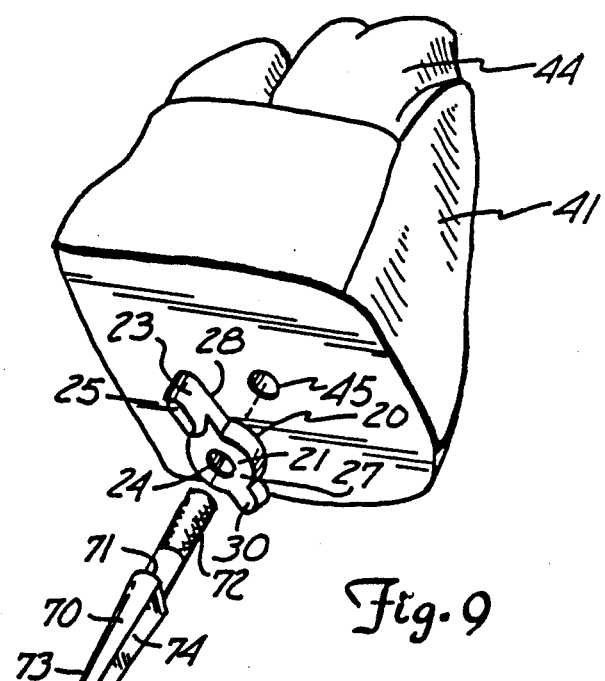
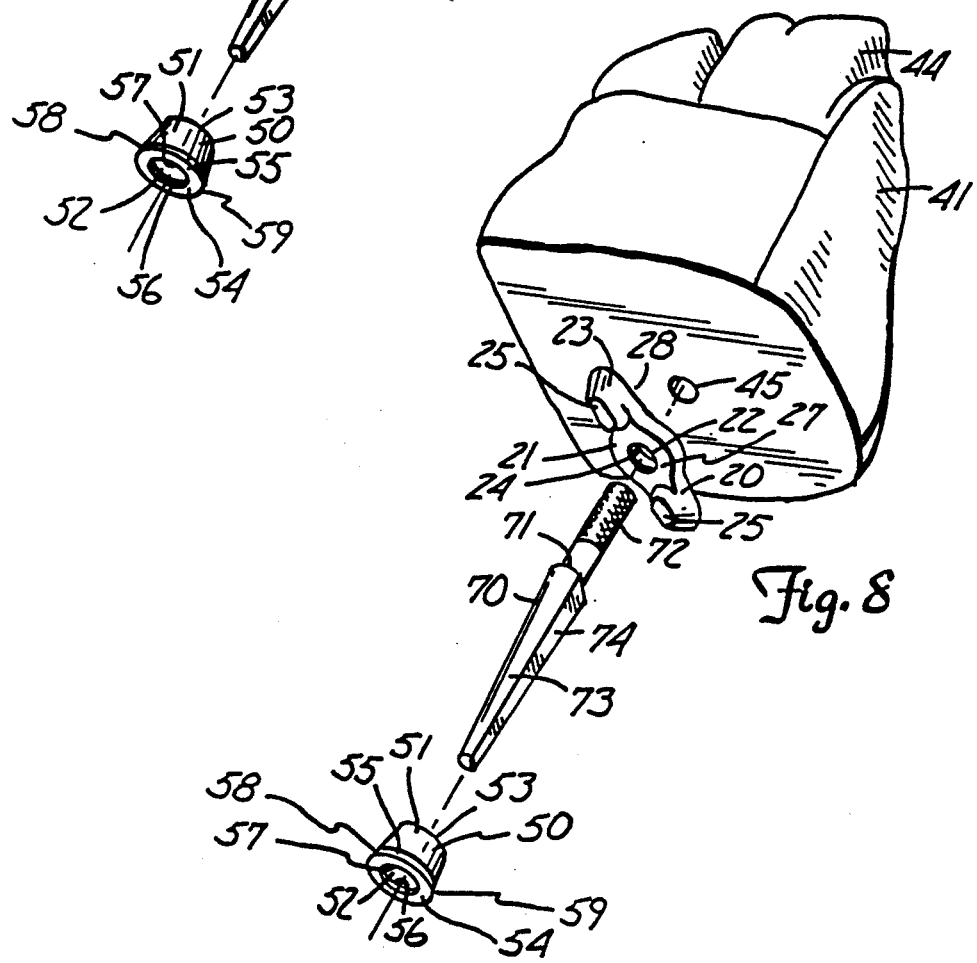

DENTAL MODEL ALIGNMENT DEVICE

This application is a continuation of application Ser. No. 140,073, filed Dec. 31, 1987, now abandoned.

FIELD OF THE INVENTION

The present invention relates generally to prosthodontic casts, and more particularly to an alignment device for aligning a dental model cast or portions thereof in a precise position relative to a base cast.

BACKGROUND OF THE INVENTION

In the dental field, it is often necessary to make a cast of a patient's teeth, a dental model, upon which dental hardware may be fabricated to fit a patient's teeth. Such a model may be made by first taking a negative impression of a patient's teeth and gums and then filling the model with a suitable casting material. After the casting material hardens, dowel pins are rigidly mounted in the dental model and a base cast is formed over the dental model. When the base cast is hardened, portions of the dental model may be separated by vertical cuts through the dental model. This enables selected portions of the dental model to be removed from the base cast so that they can be easily worked on. When the removable model portions are replaced, it is necessary to rotationally align the dental model portions with respect to the base cast so that the dental model will be stable and correspond accurately to the configuration of the patient's teeth.

Several types of dowel pins have been utilized to removably mount and rotationally align a dental model on a base cast. One such mounting device includes two parts. The first part has two differently sized dowel pins extending therefrom, and is mountable in a dental model with the dowel pins extending outwardly. The second part is mountable in a base cast and carries two appropriately sized openings for receiving the dowel pins.

Another prior art device similarly comprises a first metal part having two dowel pins, the dowel pins being receivable in a channel of a second metal part carried by a base cast. One of the dowel pins of the device is significantly shorter than the other. A similar device includes two separate dowel pins of different diameters carried by the dental model, the pins extending from the model to be received within two separate sleeves carried by a base cast.

Another prior art device comprises a single metal piece carried by a dental model having two dowel pins extending outwardly from the dental model to be received directly within two holes carried by the stone of a base cast.

Yet another prior art device includes two separate pins. One metal pin is carried by the dental model and received within an opening carried by the stone of a base cast. The other pin is made of plastic and is carried by the base cast extending outwardly, generally parallel to the pin carried by the model, the pin being receivable in an opening carried by, the dental model.

The dowel pins appearing in the prior art are generally, expensive to manufacture and often unduly complicated or cumbersome, preventing close spacing of the pins, such as for closely spaced teeth. In use, some tend to loosen in their engagement with their mating part, resulting in a loose fit between the dental model and the base cast.

SUMMARY OF THE INVENTION

The present invention relates to a dental alignment device for orienting a dental model or portion thereof with respect to a base cast. The dental model employed is of the type having a dowel pin extending from a prosthodontic cast. The alignment device comprises a collar portion adapted to receive the dowel pin and an alignment means extending radially outwardly of the collar and being receivable in a complementary depression formed in the base cast. The alignment means functions to rotationally align the dental model with respect to the base cast when the model is mounted thereon. The alignment device may include a gasket means carried by the base cast to provide a snug fit between the dowel pin and the base cast, thereby preventing fluid cast material from entering an area around the periphery of the pin inside the gasket means.

BRIEF DESCRIPTION OF THE DRAWINGS

FIG. 4 is a perspective view of an alternative embodiment of the alignment means of the invention;

FIG. 5 is a perspective view of an alternative embodiment of the alignment means of the invention;

FIG. 6 is a perspective view of an alternative embodiment of the alignment means of the invention;

FIG. 7 is a perspective view of an alternative embodiment of the alignment means of the invention;

FIG. 8 is an exploded perspective view of the dental model alignment device of the invention;

FIG. 9 is an exploded perspective view of the dental model alignment device of the invention utilizing an alternative embodiment of the alignment means.

DETAILED DESCRIPTION OF THE PREFERRED EMBODIMENT

Figure 1:
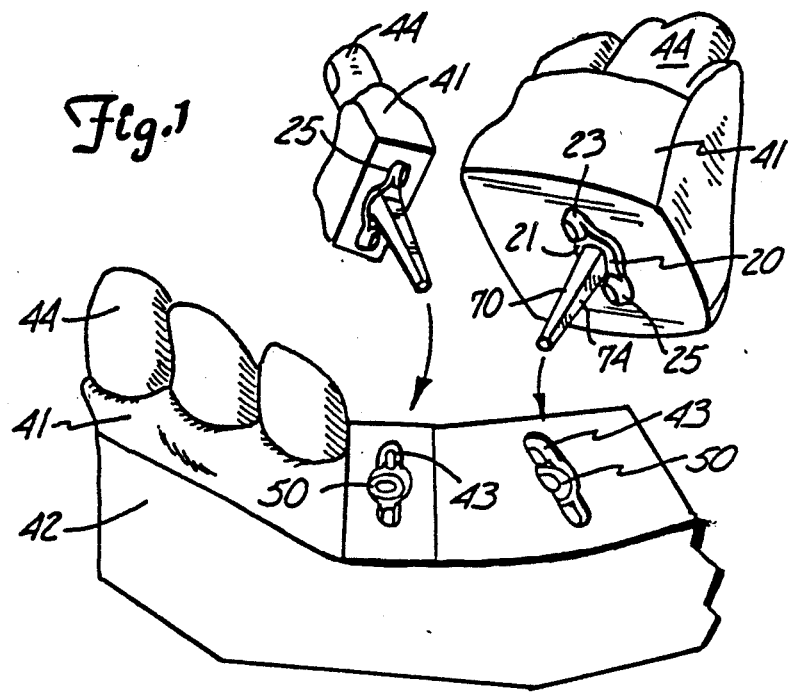
FIG. 1 is an exploded perspective view of the dental model alignment device of the invention.
Figure 10:
FIG. 10 is cross sectional view of the dowel pin and gasket means of FIG. 2 taken along line 10—10 thereof.
Figure 2:
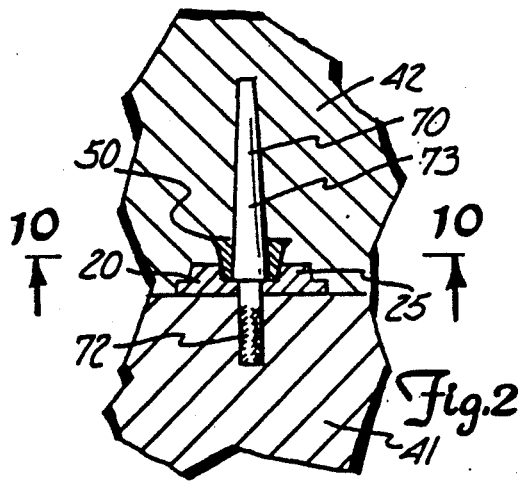
FIG. 2 is a fragmented cross-sectional view showing the engagement between the dental model, dowel pin, alignment means, and the base cast.
Figure 3:
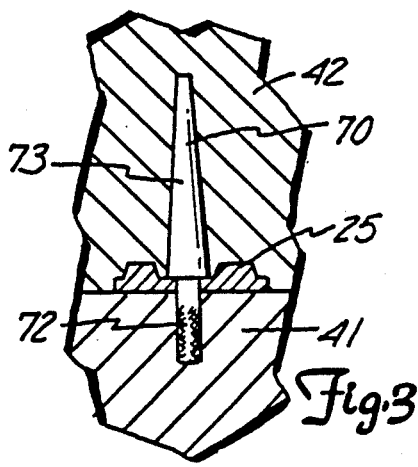
FIG. 3 is a fragmented cross-sectional view showing the engagement between the dental model, dowel pin, alignment means, gasket, and the base cast.

Referring now to the drawings, FIG. 1 shows the alignment device (20) of the invention as it is mounted on a dowel pin (70) carried by a dental model (41). The alignment device (20) includes a collar portion (21) for receiving therein the dowel pin (70), and alignment means 23) extending radially therefrom.

The collar (21), as shown in FIGS. 4–7, includes a desirably circular (or other suitably shaped) opening (22) having an axis extending through the collar (21) generally perpendicular to a flat upper surface (27) of the collar (21), the opening (22) being sized to closely receive a dowel pin (70). Preferably, the opening (22) includes a slight radially inwardly extending flange (24), shown in FIGS. 8 and 9, carried adjacent the lower surface (28) of the alignment device (20) for sealingly engaging the dowel pin (70) about its periphery. This flange is particularly useful in accommodating dowel pins (70) of slightly varying diameters.

The radially extending alignment means (23) may comprise a variety of suitable configurations, as shown in FIGS. 4–7, but desirably includes one or two portions extending radially outwardly of the collar portion (21).

Extending upwardly from at least one of the radially outwardly extending portions, generally parallel to the axis of the central opening (22), is at least one protrusion (25) having parallel or preferably upwardly converging walls (29).

An especially preferred embodiment of the alignment device (20) is shown in FIG. 4. The alignment means (23) has tapered sides (26) defining the upwardly extending protrusions (25). FIGS. 5, 6 and 7 show alternative embodiments of the invention to fit dental model pieces (41) of different shapes and spacings. The alignment device (20) shown in FIG. 5 is somewhat wider and is suitable for relatively wider spacing of model portions (41), carrying the protusions (25) on the upper surface (27) of the device. FIG. 6 shows an alternative embodiment of the invention wherein the alignment means (23) has one end with tapered side walls (26) and an upwardly directed protrusion (25) and another end with only a short extension (30). The short extension (30) generally would be oriented inwardly toward the cent of a curve defined by the teeth (44) of a model (41), thereby permitting quite close spacing of dowel pins (70). FIG. 7 shows a similar embodiment incorporating the basic design of FIG. 5. The upwardly extending protusions might also comprise hemi-spherical protusions, cylinders with generally vertical walls, or other similar configurations. Conversely, the alignment means might include a depression rather than a protrusion, thereby forming a complimentary protrusion in the base cast.

The alignment device (20) is used cooperatively with a dowel pin (70) such as that shown in FIGS. 8 and 9. The dowel pin (70) typically comprises a generally elongated Frusto conical pin, usually metal, having a first end (72) of slightly smaller diameter which may be knurled for enhanced engagement in the stone of a dental model (41). Spaced a distance from the first end (72) is a shoulder (71) extending radially outwardly, the shoulder (71) being a transition between the narrow knurled portion fixed in the dental model (41) and the wide end of the Frusto conical portion which is removably receivable in the base cast (42). The wider portion (73) tapers inwardly toward the second end of the pin to facilitate such removal, and may include a flat side (74) to largely prevent the pin (70) from rotating with respect to the base cast (42).

The device of the invention also may include a gasket (50), preferably formed of flexible plastic, having a generally cylindrical shape and a central opening (57) extending axially therethrough. The gasket (50) preferably includes first and second ends (53, 54), an outer wall (51) which preferably tapers inwardly toward the first end (53), and an inner wall (52) which is generally cylindrical. The second end (54) preferably includes a circular flange (55) extending radially outwardly of the outer surface (51) of the gasket (50) and radially inwardly of the inner surface (52) of the gasket (50). Preferably the flange (55) extends about the entire periphery of the second gasket end (54). The flange (55) may, however, include a pair of flat surfaces (58 59) oriented generally parallel to the axis of the opening (57), and generally parallel to each other on opposite sides of the gasket (50). These flat surfaces (58, 59) enable a plurality of similar gaskets (50) to be spaced more closely to one another. Preferably, the inwardly directed portion of the flange includes an inwardly directed sealing surface (56) which converges radially inwardly toward the second end (54) of the gasket (50) to sealingly engage the peripheral surfaces of a dowel pin (70) The gasket (50) is included to prevent poured stone from entering an area around the periphery of the pin (70) adjacent the gasket wall (52).

The dental model (41) and base cast (42) to be utilized with the device of the invention is made generally by the following procedure, which is well known in the art. A negative impression is made of a patient's teeth and gums. A suitable, accurate hardening stone like material is poured and vibrated into the impression to a depth of approximately three-fourths of an inch to form the dental model (41). After the stone dental model (41) hardens, it is removed from the impression and is ground flat on the surface opposite the model teeth (44). The dental model (41) is then drilled with a precision drilling machine to form holes (45) having a predetermined location, depth and diameter. The number of holes (45) that are drilled are determined by the spacing and location of the teeth (44) on the dental model (41). The holes (45) are either steam cleaned or blown out with compressed air to remove any dust or particles of stone. Dowel pins (70) are then cemented into the holes (45) following the procedure disclosed below.

As shown in FIGS. 8 and 9, the knurled end (72) of the dowel pin (70) is inserted into the opening (22) of the alignment collar (21) with the protrusions (25) on the alignment device (20) directed toward the tapered end (73) of the dowel pin. The alignment device (20) is pressed firmly onto the dowel pin (70) until its flat upper surface (27) abuts the shoulder (71) of the dowel pin (70). With the alignment device (20) in place, a suitable adhesive such as cynoacrylate is applied to the knurled end (72) of the pin (70) and to the lower surface (28 of the alignment device (20). The knurled end (72) of the pin (70) is then inserted firmly and completely into the opening (45) in the dental model (41) with the lower surface (28) of the alignment device (20) firmly contacting the exposed surface of the dental model (41). The cement is then allowed to dry. Any number of dowel pins (70) may be mounted in this manner.

After the pins (70) have been mounted in place and the cement has hardened, the gaskets (50) are placed over the dowel pins (70) with the flange (55) directed away from the dental model (41). The gaskets (50) are pressed onto the pins (70) until the first end (53) of the gasket (50) contacts the upper surface (27) of the collar (21) of the alignment device (20). Preferably, each gasket (50) placed on a pin (70) is color coded to match the color of its corresponding alignment device (20). This feature enables a user to easily determine which dental model pin (70) goes in which complimentary depression (43) of the base cast.

At this point, the areas of the dental model (41) that are to be made removable from the base cast (42) are coated on the flat surface containing the dowel pins (70) with a special separating medium which prevents a second layer of stone from adhering to the dental model (41). After the separating medium is in place, a second layer of stone is poured and vibrated onto the dental model (41) to a depth above the protruding ends of the pins (70) to form the base cast (42). After the base cast (42) has hardened, the excess stone is trimmed and the exposed bottom surface of the second layer is ground flat to expose the ends of the embedded dowel pins (70). The individual sections of the dental model (41) to be removed are then cut vertically between the dowel pins (70) with a thin coping saw blade or similar tool. The cut starts on the tooth side of the model (41) and extends down to the top surface of the base cast (42). When all of the sections to be removed have been cut, the model (41) is positioned with the teeth (44) facing downwardly and the dowel pins (70) are tapped out from the base cast (42) using a center punch or similar instrument. The removable sections are then removed and replaced into the base cast (42) to insure smooth operation. The dental model portions (41) and the base cast (42) are shown in FIG. 1.

The alignment device (20) is configured and arranged to engage a complimentary depression (43) carried by the base cast (42), corresponding to its impression formed when the second layer of stone is poured over the dental model (41) When the dowel pin (70) is firmly seated in its complimentary depression (43) in the base cast (42), the alignment means (23) prevents the pin (70) from rotating or moving laterally with respect to the base cast (42). The complementary depression (43) carried by the base cast (42) may contain a gasket (50) as previously described to grip the dowel pin (70) and retain the dental model (41) firmly in a desired position upon the base cast (42).

Dental models (41) are generally used for the fabrication of dental appliances such as caps, crowns, and bridges. These appliances may be fabricated directly on the dental model (41) and then applied to the teeth of the patient. In the fabrication process, the individual portions of the dental model (41) are removed and replaced to facilitate accessibility to particular teeth (44).

The importance of replacing the dental model (41) exactly and firmly in a desired position upon the base cast (42) becomes apparent when dental work is to be performed on adjacent teeth. In order to successfully perform this type of work, the dental model portions (41) must be held firmly and precisely in a position corresponding accurately to the positioning of the respective teeth within the mouth of the patient. If the positioning of the dental model portions (41) are even slightly altered from the positioning of the teeth of the patient, the dental apparatus being fabricated upon the model (41) may not fit the patient's teeth. The device of the invention enables particular portions of the dental model (41) to be removed from the base cast (42) and then easily replaced in their respective positions accurately in alignment with one another.

While a preferred embodiment of the present invention has been described, it should be understood that various changes, adaptations and modifications may be made therein without departing from the spirit of the invention and the scope of the appended claims.

What is claimed is:

1. An alignment device for orienting a dental model which is removably mountable to a base cast, the model being of the type having a dowel pin extending from a prosthodontic cast, comprising a collar portion adapted to receive the dowel pin, and alignment means extending radially outwardly of the collar and being receivable in a complimentary depression formed in the base case to rotationally align the dental model with respect to the base cast when the model is mounted thereon, the alignment means being of a generally narrow width with respect to the collar portion and having a longitudinal axis and upper and lower surfaces, and further including at least one protrusion extending upwardly from the upper surface, generally perpendicular to the longitudinal axis, the protrusion being carried adjacent an end of the alignment means.

2. An alignment device for orienting a dental model which is removably mountable to a base cast, the model being of the type having a dowel pin extending from a prosthodontic cast, comprising a collar portion adapted to receive the dowel pin, alignment means extending radially outwardly of the collar and being receivable in a complimentary depression formed in the base cast to rotationally align the dental model with respect to the base cast when the model is mounted thereon, the alignment means being of a generally narrow width with respect to the collar portion, and gasket means for receiving the dowel pin in the complimentary depression carried by the base cast to provide a snug fit between the dowel pin and the base cast, the gasket means including a radially inwardly extending, resilient flange for sealing against the dowel pin, thus preventing fluid cast material from entering an area around the periphery of the pin inside the gasket means.

3. The device of claim 2 wherein the gasket means comprises a generally cylindrical gasket having an axis, a central opening extending therethrough, and inner and outer surfaces, a first end of the gasket including a generally circular flange extending radially outwardly of the outer surface of the gasket and radially inwardly of the inner surface of the gasket for sealingly engaging the dowel pin.

4. The device of claim 3 wherein the portion of the flange extending radially inwardly of the inner surface of the gasket carries an inwardly directed sealing surface which tapers radially inwardly toward the first end of the gasket.

5. The device of claim 3 wherein the gasket includes walls that are thicker in cross-section at the first end than at the second end so that the outer surface of the walls tapers radially inwardly toward the second end.

6. The device of claim 3 wherein the portion of the flange extending radially outwardly of the outer surface of the gasket includes a pair of flat surfaces carried generally on opposite sides of the flange and parallel to each other, to enable the gaskets to be carried adjacent one another by closely spaced complimentary depressions carried by the base cast.

7. The device of claim 3 wherein the alignment means and the gasket are formed of plastic and are color coded to enable a user to identify and match the dental model corresponding to a particular complimentary depression in the base cast.

8. An alignment device for orienting a dental model which is removably mountable to a base cast, the model being of the type having a dowel pin extending from a prosthodontic cast, comprising:

a collar portion adapted to be fixedly secured to the dowel pin, the collar portion including an opening having an axis for receiving the dowel pin therein;

alignment means extending radially outwardly of the collar and being receivable in a complimentary depression in the base cast to rotationally align the dental model with respect to the base cast when the model is mounted thereon, the alignment means having a longitudinal axis generally perpendicular to the axis of the collar portion, upper and lower surfaces, and one or more upwardly extending protrusions, the alignment means being relatively narrow with respect to the collar portion to allow the device to be carried by closely spaced dowel pins, and gasket means associated with the complimentary depression in the base cast for receiving the dowel pin therein to provide a snug fit between the dowel pin and the base cast, thereby preventing fluid cast material from entering an area around the periphery of the pin inside the gasket means, the gasket means comprising a generally cylindrical gasket having an axis, a coaxial central opening extending therethrough, and inner and outer surfaces, a first end of the gasket including a generally circular flange extending radially outwardly of the outer surface of the gasket and radially inwardly of the inner surface of the gasket for sealingly engaging the dowel pin, the gasket including walls thicker in cross section at the first end than at a second end, the outer surface of the walls tapering radially inwardly toward the second end, the alignment means and the gasket being color coded to enable a user to identify and match the dental model corresponding to a particular complimentary depression in the base cast.

* * * * *